United States Patent [19]

Lewis, deceased

[11] 3,956,483

[45] May 11, 1976

[54] PREPARING PANCREATIN

[75] Inventor: Sheldon H. Lewis, deceased, late of Chicago Heights, Ill., by Barbara Lewis, administratrix

[73] Assignee: Wilson Pharmaceutical & Chemical Corporation, Chicago, Ill.

[22] Filed: May 17, 1971

[21] Appl. No.: 144,230

Related U.S. Application Data

[63] Continuation of Ser. No. 770,443, Oct. 24, 1968, abandoned.

[52] U.S. Cl. ................................ 424/94; 424/110
[51] Int. Cl.² ........................................ A61K 37/48
[58] Field of Search ............... 424/94, 110; 195/63, 195/68

[56] References Cited
UNITED STATES PATENTS

| | | | |
|---|---|---|---|
| 1,590,388 | 6/1926 | Lepetit | 195/68 X |
| 2,567,747 | 9/1951 | Wallerstein | 195/63 |
| 3,019,171 | 1/1962 | Bloch et al. | 195/63 X |
| 3,223,594 | 12/1965 | Hock | 195/68 |

OTHER PUBLICATIONS

Wilson et al., Textbook of Organic Medicinal and Pharmaceutical Chemistry, 1962, 4th Edition, pp. 762–764.

*Primary Examiner*—Norman A. Drezin

[57] ABSTRACT

The invention deals with compositions having utility as digestive aids. Such compositions can be produced in a dry powder form, with amylotic and lipolytic activity in addition to the proteolytic activity normally present and with harmful bacteria eliminated therefrom by treating comminuted pancreas with aqueous medium containing calcium sulfate or calcium acetate, adding a proteolytic enzyme activator and after a period required for enzyme activation, dehydrating the mixture at temperatures which will inactivate pathogenic bacteria.

4 Claims, No Drawings

PREPARING PANCREATIN

This application is a continuation of application Ser. No. 770,443, filed Oct. 24, 1968, now abandoned, entitled PANCREATIN COMPOSITION AND METHOD OF PREPARATION, now This invention relates to a method of preparing pancreatin having high amlolytic, proteolytic and lipolytic activites and of eliminating harmful bacteria therefrom while maintaining said activities.

The exocrine portion of the pancreas gland secretes a slightly alkaline liquid into the pancreatic duct and ultimately into the duodenum. This pancreatic juice which is carried to the duodenum comprises trypsinogen and chymotrypsinogen which, when activated, cause the hydrolysis of proteins into peptides; amylase, which changes amylose into dextrins and sugars; and lipase, which converts fats into their constituent molecules of glycerol and fatty acids. The trypsinogen is activated by a secretion of the duodenum called enterokinase. Chymotrypsinogen is, in turn, activated by trypsin. The diastatic and lipolytic enzymes are essentially autoactivating when secreted in the body.

Pancreatin consists essentially of dried, defatted pancreas. Pancreatin is a cream colored, amorphous powder which has a faint, characteristic but not offensive odor. Pancreatin is prepared from fresh or fresh-frozen pancreas, generally of procine origin, although beef pancreas may also be used, but is less potent. Normally the pancreas glands are minced and comminuted with porcine duodenum, which is added to activate the proteolytic enzymes in the pancreas. Alternatively, proteolytic activity is sometimes established in the pancreatin preparation by the addition of active trypsin. The blend is held at a relatively cool temperature for several days to allow the activation to occur. Thereafter, the pancreas is degreased and dried, generally by vacuum drying at room temperature.

Because of its direct influence on digestion, pancreatin finds use in many parts of the world as a digestive aid. In addition, pancreatin is used as a therapeutic agent for humans suffering from a deficiency of pancreatic enzymes in the intestine which can be caused by chronic relapsing pancreatitis or mucoviscidosis. Because the effectiveness of pancreatin in treating those suffering from pancreatic deficiencies depends upon its activity, minimum standards of activity have been established. The National Formulary provides that pancreatin convert not less than 25 times its weight of N.F. potato starch reference standard into soluble carbohydrates, and not less than 25 times its weight of casein into proteoses. See the National Formulary XII, page 287, and the First Supplement thereto, page 13. Although the National Formulary does not set forth a minimum standard for lipolytic activity, and commercially-available pancreatin has variable and often small amounts of active lipase, it of course would be desirable to have pancreatin of high lipolytic activity as well.

The addition of calcium ions to pancreatic enzymes to enhance their activity has been known for many years. See, for example, 40 *Biochimica et Biophysica Acta* 481–490 (1960) as concerns lipase; J. H. Northrop et al. *Crystalline Enzymes* 133 (2d ed. 1948) concerning trypsinogen; 16 *Federation Proceedings*, American Society of Biological Chemists 254–255 (March 1957) concerning amylase. This phenomenon has been explained in terms of some function of the calcium ion which, in the experimental descriptions given, was derived from calcium chloride. Thus, it is reported by Tauber, *Chemistry and Technology of Enzymes*, 26 (1949) that pancreatic lipase is strongly activated by calcium chloride. The same author at page 147 describes the autocatalytic conversion of trypsinogen into trypsin in the presence of calcium ion provided by the addition of calcium chloride. The autocatalysis of trypsinogen in the presence of 0.02 M $CaCl_2$ is further described by Dixon and Webb, *Enzymes*, 546 (1958). Accordingly, it would appear to one of ordinary skill in the art that calcium chloride would be effective in activating pancreatin. Contrary to such expectations, however, the present inventor has found that calcium chloride produces pancreatin of neither minimum amylolytic activity nor of measurable lipolytic activity. Since a soluble salt did not produce the results desired, a highly insoluble calcium salt, calcium hydroxide, was tried. $Ca(OH)_2$ has a solubility of 0.185 parts in 100 parts water at 0°C compared to a solubility of 59.5 parts for $CaCl_2$ (hydrophilite), according to Lange, *Handbook of Chemistry* [Revised Tenth Edition (1967)]. As shown in Table I, the activities produced by calcium hydroxide, while perhaps slightly better than those produced by calcium chloride, were not adequate for commercial purposes. Thus, it appeared unlikely that there existed a calcium salt which could enhance the activity of pancreatin, and it was evident that, even if there existed such a salt, solubility — contrary to normal expectations — was not a basis for predicting which salt that one might be.

TABLE I

| Percent Salt by Wt. Pancreas | Salt | Amylolytic Activity | Proteolytic Activity | Lipolytic Activity |
|---|---|---|---|---|
| 3.06[1] | $CaCl_2$ | Nil | 1:131 | Nil |
| 2.04[1] | $Ca(OH)_2$ | 1:25 | 1:85 | 1180 units/gram |
| 4.35[1] | $Ca(CH_3COO)_2.H_2O$ | 1:150 | 1:146 | 3150 units/gram |
| 0.747[2] | $CaSO_4.2H_2O$ | 1:193 | 1:192 | 3380 units/gram |

[1]This percentage corresponds to the addition of 25 cc of 5M salt solution or suspension to one pound (454 grams) of pancreas.
[2]This percentage is near the limit of solubility of calcium sulfate.

The tests referred to in Table I were carried out on hog pancreas activated with duodenum, defatted and vacuum dried at room temperature. The procedures followed in determining the amylolytic and proteolytic activities were the standard assays for starch and casein digestive power prescribed by the National Formulary, supra.

As used herein, one unit of lipase activity will liberate an amount of fatty acid equivalent to one cc of 0.05 N alcoholic NaOH from one cc of olive oil under the following conditions: The pancreatin to be tested is dissolved in cold, distilled water, and, if necessary, homogenized in a Waring-type blender for about one minute. The sample solution is made up to contain an amount of pancreatin which is estimated to correspond to one unit of activity per cc. (Sample solutions have been found to be stable for at least two hours when stored in a refrigerator.) Of the sample solution, portions in the amounts of 0.4, 0.6, and 0.9 cc respectively are pipetted into 100 cc flasks and the volume of liquid in each flask is adjusted to 1 cc with distilled water. A reagent blank is also set up using 1 cc of distilled water. Five cc of 0.5% bile salts in a pH 7.8 phosphate buffer is then added to each flask. The phosphate buffer is formed by dissolving 4.54 grams of monobasic potassium phosphate ($KH_2PO_4$) in sufficient water to make 500 ml of solution, and by dissolving 4.73 grams of anhydrous dibasic sodium phosphate ($Na_2HPO_4$) in sufficient water to make 500 ml of solution; from the resulting solutions, 10 cc of the monobasic potassium phosphate solution are mixed with 90 cc of dibasic sodium phosphate solution. The pH is then checked and adjusted to pH 7.8. The bile salts solution is formed by dissolving 0.500 grams of Extract of Ox Bile, N.F. powder in a sufficient volume of pH 7.8 phosphate buffer to make 100 ml of solution.

To each flask is then added 1 cc of olive oil U.S.P., delivered by means of a 1 cc syringe. The mixture is then shaken at 37°C for 30 minutes at approximately 200 vibrations per minute. After the digestion period, there is added to each flask 5 drops of concentrated HCl to stop the enzymatic action, then 20 cc of benzene (Reagent Grade, thiophene free). The flasks are swirled for one minute, then allowed to stand until the two phases separate. A 10 cc aliquot of the upper benzene layer is pipetted into a 50 ml Erlenmeyer flask, then 1 cc of methyl alcohol and 3 drops of phenolphthalein indicator are added to each flask. The contents of the flask are titrated with 0.05 NaOH in methyl alcohol. The titration volume is recorded for each level of unknown and for the blank.

The lipase activity for each unknown sample is calculated by dividing twice the difference between the volume titrated into the unknown and the volume titrated into the blank by the weight in grams of the sample in each digestion flask. The three values obtained should agree within five percent of the average to indicate linearity of response. The average of the three values is used to designage potency, and is expressed in units per gram.

A further shortcoming in the art of preparing pancreatin is that no way of reliably eliminating harmful bacteria, particularly those of the genus Salmonella, has been developed. It is possible to inactivate these pathogenic bacteria by heating the pancreatin to a sufficiently high temperature. Heretofore, however, the unfortunate result of such a heating step was a substantial deactivation, e.g. 90%, of the pancreatic enzymes.

Accordingly, it is an object of this invention to provide a method or preparing pancreatin which results in a product having high proteolytic, amylolytic, and lipolytic activities.

Another object is to provide a method of preparing pancreatin which is free of harmful bacteria and which also has high proteolytic, amylolytic, and lipolytic activities.

TABLE II

| Type of Pancreas | Percent Salt By Wt. of Pancreas | Salt | Amylolytic Activity | Proteolytic Activity | Lipolytic Activity |
|---|---|---|---|---|---|
| Pork | 0.72 | $CaSO_4.2H_2O$ | 1:193 | 1:142 | 2230 units/gram |
| Pork | 0.02 | $CaSO_4.2H_2O$ | 1:220 | 1:136 | 1980 units/gram |
| Pork | 1.4 | $Ca(CH_3COO)_2.H_2O$ | 1:175 | 1:159 | 2200 units/gram |
| Beef | 0.72 | $CaSO_4.2H_2O$ | 1:35 | 1:74 | <1000 units/gram |
| Beef | 0.72 | $Ca(CH_3COO)_2.H_2O$ | 1:18 | 1:67 | <1000 units/gram |

The present inventor has found that excellent results in activating pancreatin are achieved with calcium sulfate, which is nearly insoluble in water, and with calcium acetate, which is nearly as soluble as calcium chloride. The solubility of $CaSO_4.2H_2O$ is 0.223 parts in 100 parts water at 0°C and the solubility of $Ca(C_2H_3O_2).H_2O$ is 52 parts in 100 parts water at 0°C. Lange, supra. As may be seen from Table I, under the test conditions set forth above, the presence of either calcium sulfate or calcium acetate produced amylolytic and proteolytic activity 6 to 8 times NF strength (1:25) and provided outstanding lipolytic activity.

Completely surprising and wholly without explanation is the fact that not only does either calcium sulfate or calcium acetate enhance the activity of pancreatin, but material containing either salt can be heated to a temperature high enough to inactivate pathogenic bacteria without a substantial loss of activity. Table II shows the activities of three samples of pork pancreatin prepared from a single batch of hog pancreas and two samples of beef pancreatin from a single batch of beef pancreas which contained calcium sulfate or calcium acetate and which had been heated at 180°F (82°C) for 16 hours in a vacuum drying oven.

It may further be seen from the second example in Table II that calcium sulfate in an amount equal to 0.02% by weight of pancreas produced activities which on the whole were somewhat lower than those produced by 0.72% calcium sulfate. While 0.02% is not to be construed as a minimum, it is believed that concentrations below this value will not consistently produce the results desired. As will be understood by those skilled in the art, the potency of the pancreatin is to a large extent dependent upon the quality of the starting material. Accordingly, it may be possible to adequately activate very high quality pancreas with less than 0.02% calcium sulfate and conversely pancreas of poor quality may require significantly larger amounts of the salt. It should be further pointed out that 0.02% corresponds to 200 parts per million or one tenth of a gram per pound. When considering that pancreatin is generally prepared in lots of several hundred pounds, extra difficulty may be encountered in attempting to uniformly combine qualities less than a tenth of a gram per pound; therefore, the statements made herein that the method comprises the addition of at least about 0.02% of calcium sulfate or calcium acetate by weight of pancreas should be construed in the light of the preceding remarks.

Typically, pancreatin is prepared from fresh or fresh-frozen pancreas of porcine origin. The pancreas glands are comminuted to a particle size of about ⅛ inch to about ¼ inch in cross-section, although larger or smaller particles may be present. Comminuted porcine duodenum in an amount equal to about 10% of the weight of the pancreas is added to activate the proteolytic enzymes. In accordance with the method of the present invention, calcium sulfate or calcium acetate is added in an amount equal to at least about 0.02% by weight of the pancreas. It has been found that a preferred range of concentration of calcium sulfate is 0.35 to 0.77% by weight of the pancreas. Calcium acetate can advantageously be added in somewhat higher concentrations.

Acetone is frequently added to the activation mixture in order to increase its fluidity and because acetone exerts a beneficial bacteriostatic action during the processing steps. The activation blend of pancreas, duodenum, and calcium sulfate or calcium acetate is held at a temperature of from 0° to 27°C (32° to 80°F) for from 6 hours to several days, depending upon the temperature used. Very commonly, the activation is carried out at about 4°C (40°F) for 70 hours. Of course, the mixture may be monitored at regular intervals to determine when appropriate activation has been achieved. After the activation is complete, the pancreas is degreased by use of any conventional method, for example, washing with acetone. Wholly unexpectedly, it has been found that the degreased pancreas containing calcium sulfate or calcium acetate can be exposed to a temperature sufficient to inactivate pathogenic bacteria therein, particularly those of the genus Salmonella, without significant loss of activity. Accordingly, the tissue may finally be dried at a temperature sufficient to inactivate pathogenic bacteria, which temperature is generally in excess of 160°F (73°C) and preferably at 180°F (82°C). Alternatively, after a heating step to kill harmful bacteria, the material may be lyophilized. Thereafter, the dried tissue is finely comminuted, or milled, to a specified particle size and packaged for sale, or is collected for further processing such as the extraction of specific enzymes.

The features, principles, and advantages of the invention will be more fully understood from a consideration of the following examples.

EXAMPLE I

To 700 pounds (318 kilograms) of hashed pork pancreas were added 2,275 grams (5.02 pounds) — 0.716% by weight — of $CaSO_4.2H_2O$ slurried in 17.5 liters (4.62 gallons) of deionized water. After the calcium sulfate slurry was thoroughly mixed into the pancreas, 70 pounds (31.8 kilograms) of hashed pork duodenum were added and thoroughly mixed therein. Finally 17.5 gallons (66.3 liters) of acetone (C.P. grade) were thoroughly combined with the mixture. The mixture was then stored for 7 days at a temperature of 38° to 40°F (about 4°C) in order to complete activation. Thereupon, the pancreatin was defatted by washing the wet, fatty mass with a sufficient number of washes of room-temperature acetone to dehydrate and degrease the tissue. The acetone-wet tissue was then heated under vacuum until the temperature of the material reached 180°F (82°C). The vacuum was then released and the temperature of the material maintained at 180°F (82°C) under atmospheric pressure for three hours. The material was exposed to the atmosphere during this step because the moisture in the air promotes the destruction of Salmonella bacteria. Thereafter, the vacuum drying oven was cooled to 120°F (49°C) and maintained at that temperature under vacuum for one hour. Thereupon the dried pancreas was removed from the dryer and collected for the particle comminution or milling operation. The standard assays for activity identified above disclosed that this dried material had an amylolytic activity of 1:175, a proteolytic activity of 1:159, and a lipolytic activity of 2210 units/grams. Tests for Salmonella bacteria, which were of a kind approved by the U.S. Food and Drug Administration, were entirely negative.

EXAMPLE II

Two 700-pound samples were taken from a single lot of pork pancreas. To one sample were added 2,275 grams (5.02 pounds) — 0.716% by weight — of $CaSO_4$ $2H_2O$ slurried in 17.5 liters (4.62 gallons) of deionized water. No salt was added to the second sample. Both samples were then processed as described in EXAMPLE I, except that the temperature of both samples was maintained at 180°F (82°C) under atmospheric pressure for 6 hours. The results of the three standard assays, presented in Table III, show that the sample without calcium sulfate had about 20% less proteolytic and lipolytic activity and about 5% less amylolytic activity.

TABLE III

| Activity | Pancreatin with Calcium Sulfate | Pancreatin without Calcium Sulfate |
|---|---|---|
| Proteolytic | 1:190 | 1:158 |
| Lipolytic | 2910 | 2320 |
| Amylolytic | 1:208 | 1:200 |

While a basic mode of practicing the invention, together with modifications thereof, has been described in detail, various further modifications may be made by one of ordinary skill in the art to adapt the invention to individual processing needs and particular qualities of starting material without departing from the spirit and scope of the present invention, as defined in the appended claims.

What is claimed is:

1. The method of preparing in dry powder form a therapeutic pancreatin composition having proteolytic, amylolytic and lipolytic activity which comprises adding to comminuted pork or beef pancreas with thorough mixing an aqueous medium containing calcium sulfate in an amount between 0.02% and 1.4% based upon the weight of comminuted pancreas, said aqueous medium incorporating added water in an amount up to about 5.5%, based upon the weight of comminuted pancreas, admixing proteolytic enzyme for trypsinogen and chymotrypsinogen selected from the group consisting of pork duodenum and trypsin in the pancreas whereby proteolytic activity is established, maintaining said admixture at a temperature of about 32°F. to 80°F. until activation is complete, washing said admixture with acetone and heating said washed admixture to a temperature in the range between 120°F. and 180°F. whereby the admixture is dehydrated and susceptible pathogenic bacteria are inactivated.

2. The method of preparing in dry powder form a therapeutic pancreatin composition having proteolytic, amlolytic and lipolytic activity which comprises adding to comminuted beef or pork pancreas with thorough mixing an aqueous medium containing an inorganic salt selected from the group consisting of calcium sulfate and calcium acetate in an amount between 0.02% and 1.4% based upon the weight of comminuted pancreas, said aqueous medium incorporating added water in an amount up to about 5.5% based upon the weight of comminuted pancreas, admixing comminuted pork duodenum with said pancreas mixture in an amount of about 10% based upon the weight of comminuted pancreas, maintaining said admixture at a temperature of about 32°F. to 80°F. until activation is complete, washing said admixture with acetone, heating said washed admixture to a temperature in the range between 120°F. and 180°F. whereby the admixture is dehydrated and susceptible pathogenic bacteria are inactivated.

3. A method according to claim 1 wherein said activator is active trypsin.

4. A dry powdered therapeutic composition free of pathogenic bacteria and having proteolytic, amylolytic and lipolytic activity prepared by the process of claim 1.

* * * * *